United States Patent [19]

Melhart

[11] 4,323,080

[45] Apr. 6, 1982

[54] ANKLE STRESS MACHINE

[76] Inventor: Albert H. Melhart, 1007 S. 296th Pl., Federal Way, Wash. 98003

[21] Appl. No.: 161,915

[22] Filed: Jun. 23, 1980

[51] Int. Cl.³ .............................................. A61B 6/00
[52] U.S. Cl. .................................. 128/774; 269/328; 128/133; 128/782
[58] Field of Search ............. 128/774, 779, 782, 25 R, 128/133; 269/328; 248/349; 312/252, 305

[56] References Cited

U.S. PATENT DOCUMENTS

| T100,602 | 5/1981 | Roley et al. | 128/782 |
|---|---|---|---|
| 2,351,293 | 6/1944 | Saunders | 248/349 |
| 2,923,289 | 2/1960 | Carson | 128/25 R |
| 3,063,714 | 11/1962 | Krauss | 248/349 |
| 3,521,876 | 7/1970 | Smith | 269/328 |
| 3,752,144 | 8/1973 | Weigle, Jr. | 269/328 |
| 4,045,678 | 8/1977 | Rickard | 269/328 |
| 4,062,355 | 12/1977 | Kaye . | |
| 4,202,355 | 5/1980 | Loeffler | 128/774 |
| 4,232,681 | 11/1980 | Tulaszewski | 128/653 |
| 4,236,528 | 12/1980 | Stanec et al. | 128/741 |

FOREIGN PATENT DOCUMENTS

| 681655 | 7/1939 | Fed. Rep. of Germany | 128/774 |
|---|---|---|---|
| 858452 | 7/1949 | Fed. Rep. of Germany | 128/774 |

OTHER PUBLICATIONS

Rastegar, J. et al., Apparatus for Measuring Load-Displacement and Load-Dependent Kinematic Characteristics of Articulating Joints-Application to the Human Ankle Joint, J. Biomedical Eng., vol. 102, Aug. 1980, No. 3, pp. 208-213.

Primary Examiner—Robert W. Michell
Assistant Examiner—Nancy A. B. Swisher
Attorney, Agent, or Firm—Christensen, O'Connor, Johnson & Kindness

[57] ABSTRACT

An ankle stress machine particularly suited for use in the X-ray examination of ankles is disclosed. The ankle stress machine includes a planar base (11) having an aperture (12) near one end suitable for receiving a standard X-ray cassette (14). Mounted on the base (11) is a calf restraining mechanism (13). The calf restraining mechanism (13) supports the calf of a patient in a horizontal position and includes braces for preventing lateral horizontal movement in at least one direction. Mounted on the base (11) above the cassette aperture (12) is a turntable (15). Mounted atop the turntable (15) is a foot support and stress assembly (17) that includes a foot cup (93) and a radial arm (75). The foot cup (93) is vertically oriented and receives the foot of a patient. The foot cup conforms to the heel of the patient's foot, and encloses the bottom and sides of the foot between the heel and the end of the metatarsal bones of the largest foot to be accommodated. The radial arm (75) is attached to the foot cup and rotates it with respect to the base via the turntable (15). The radial arm (75) is connected to a measuring device (19) that measures the stress applied to the arm when it is used to rotate the foot cup and stress the ankle of a patient. After the ankle is stressed, an X-ray source (111) mounted above the ankle exposes the portion of an X-ray cassette (14) mounted in the cassette aperture (12) in the base and, thereby, creates an image of the stressed ankle. Two side-by-side comparison images can be created by exposing one-half the cassette (14) when an injured ankle is stressed and exposing the other half when the uninjured ankle is stressed.

16 Claims, 3 Drawing Figures

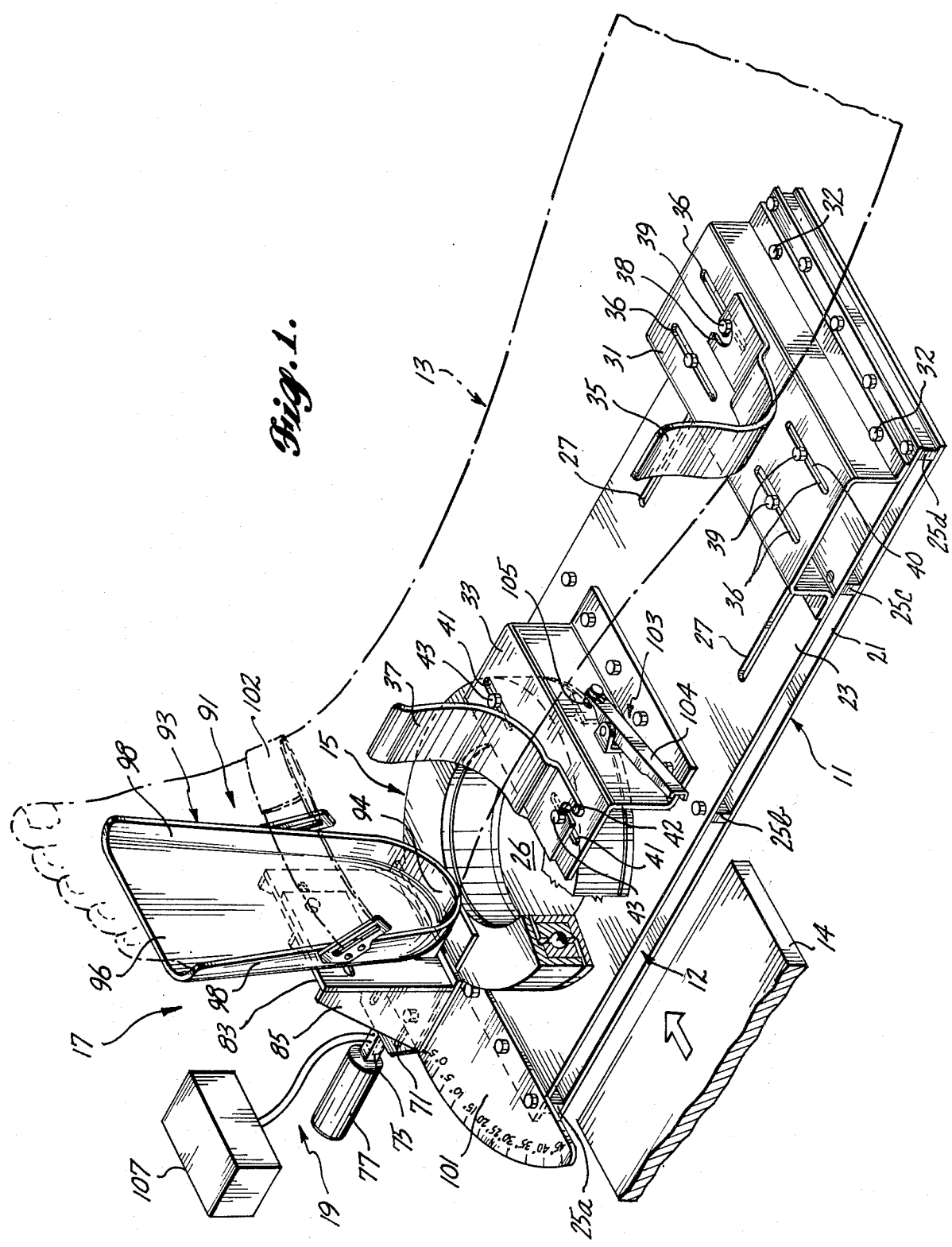

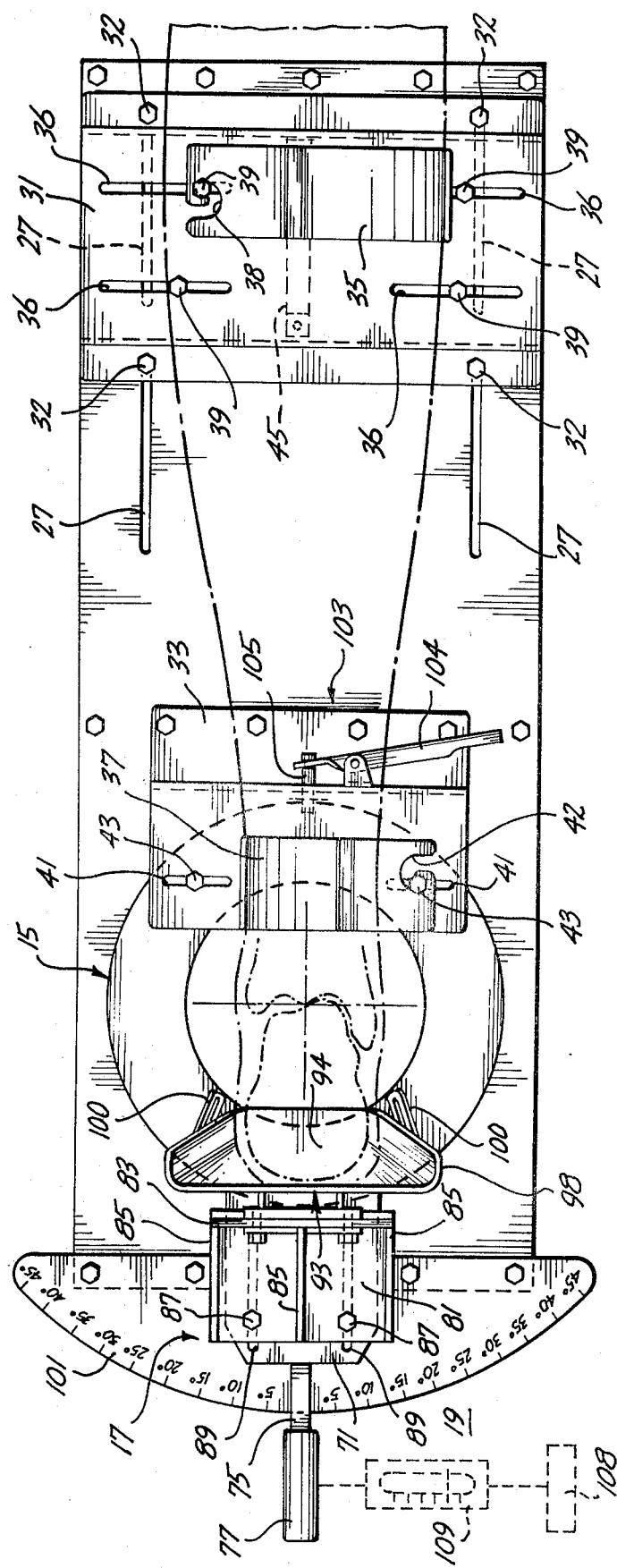

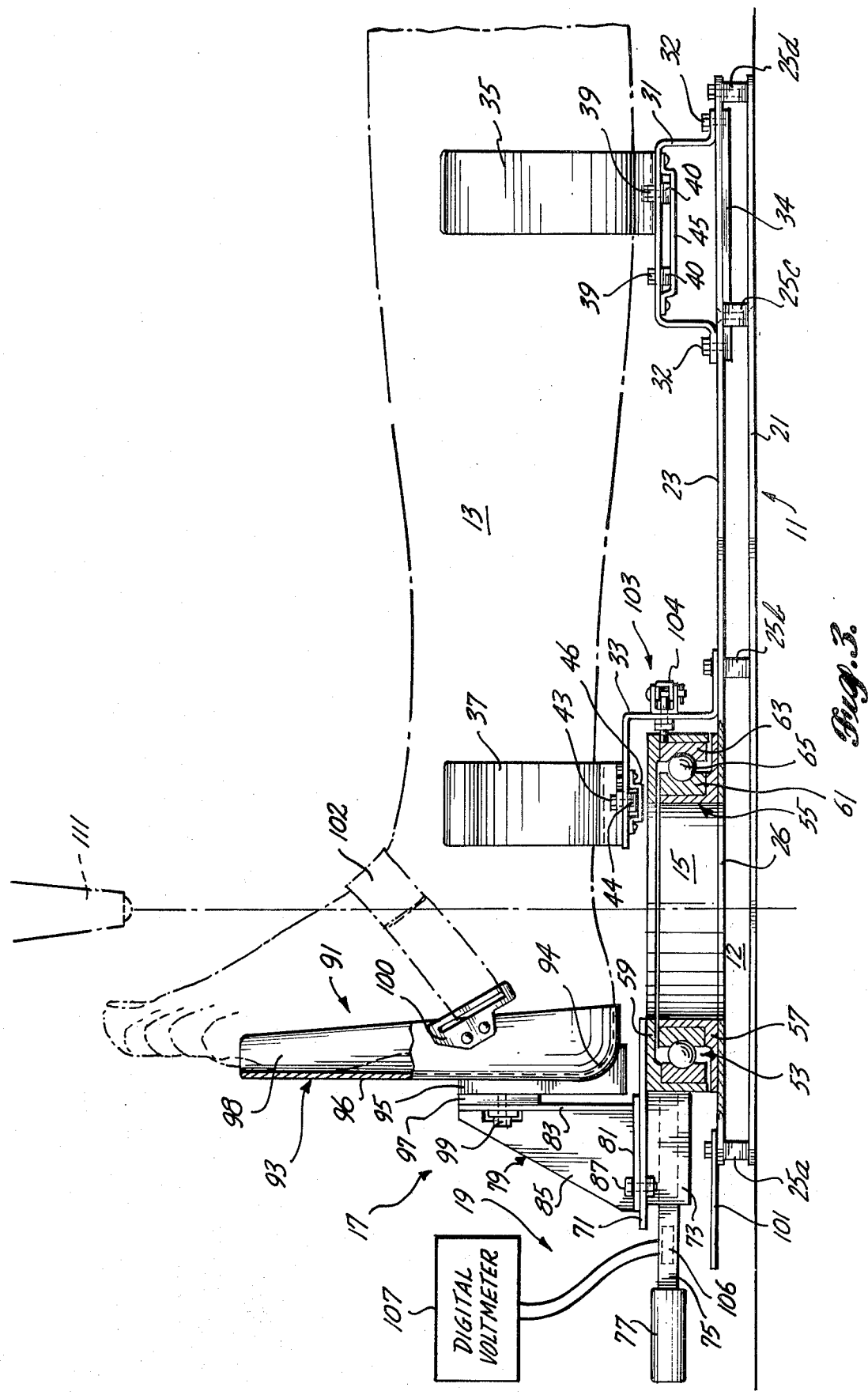

ANKLE STRESS MACHINE

TECHNICAL AREA

This invention is directed to orthopedic devices and, more particularly, orthopedic devices for stressing the joints of the human body.

BACKGROUND OF THE INVENTION

When an ankle is injured, even a highly skilled orthopedic physician cannot determine merely from observation whether the injury is a sprain, pulled ligaments, a fracture or a combination thereof. As a result, the orthopedic physician normally has the ankle X-rayed to assist him in determining the extent and exact nature of the ankle injury. Such X-rays become significantly more meaningful if the ankle is stressed by rotating the foot inwardly (inversion) and/or outwardly (eversion) when the X-ray pictures are taken, and then compared to the X-rays of the patient's unstressed ankle. In the past, ankle stressing has been accomplished by having one person manually stress the ankle by supporting the calf with one hand and rotating the foot in the desired direction with his other hand while a technician takes an X-ray picture of the stressed foot. Obviously this procedure has a number of disadvantages. For example, it exposes the ankle stressing person, due to his proximity to the ankle of the patient, to an undesirable amount of X-radiation. Secondly, it is difficult, if not impossible, for a person to manually, repetitively apply exactly the same amount of stress to an ankle. However, identical stress application is important where it is desirable to compare bone separation in the injured ankle with bone separation in the uninjured ankle to assist in determining the extent of ankle injury, for example. In this regard, it has been found that the angular amount of inward and outward ankle rotation that occurs when the same stress is applied varies from patient to patient. Consequently, merely rotating the ankle by a predetermined angle provides insufficient information for X-ray comparison purposes. That is, because some ankles will be significantly stressed and others lightly stressed when an ankle is rotated through the same angular amount, angular readings are an inadequate indication of ankle stress. Yet is is ankle stress that is important in determining the nature and extent of ankle injuries. As a result, machines of the type disclosed in U.S. Pat. No. 3,521,876 entitled BODY MEMBER SUPPORT FOR X-RAY EXAMINATION, by Jeffery P. Smith, are generally unsuitable for use in obtaining X-rays showing the affect of a known amount of stress on an ankle. Obviously, it would be desirable to provide a machine for stressing an ankle such that the ankle can be X-rayed in a stressed position, particularly such a machine that allows the stressing person to move away from the source of X-radiation and, thus, limit his exposure.

Therefore, it is an object of this invention to provide an ankle stress machine.

It is another object of this invention to provide an ankle stress machine suitable for use in connection with X-ray equipment so that the ankle can be X-rayed in a stressed position.

It is a still further object of this invention to provide an ankle stressing machine suitable for use in X-ray equipment to stress the ankle in a manner that allows the stressing person to move away from the source of X-radiation during the X-ray taking procedure.

SUMMARY OF THE INVENTION

In accordance with this invention, an ankle stress machine ideally suited for use in the X-ray examination of ankles is disclosed. The ankle stress machine includes a base that supports a calf restraining mechanism and a turntable. The turntable supports a foot support and stress assembly. A patient's foot is horizontally supported by the calf restraining mechanism and prevented from horizontal movement in one direction or the other (depending upon the adjustment of the machine) in a horizontal plane. When suitably positioned, the foot of the patient rests in a foot cup that forms part of the foot support and stress assembly. The foot support and stress assembly also includes an arm used to manually rotate the foot cup about the axis of rotation of the turntable. The foot cup is formed such that it encloses the bottom and the inner and outer edges of the foot from the heel to the upper end of the metatarsal bones of the largest foot expected to be accommodated by the ankle stress machine.

In operation, a patient's foot is mounted in the ankle stress machine such that his calf is restrained by the calf restraining mechanism and foot lies in the foot cup. Thereafter, the arm is used to manually rotate the foot cup with respect to the base, via the turntable. As a result, stress is applied to the ankle. The amount of stress is measured by a suitable mechanical or electronic force measuring device.

In accordance with other aspects of this invention, preferably, the turntable is formed of a ball bearing assembly having an aperture large enough to circumscribe the ankle of a patient. The ball bearing assembly is mounted atop the base. In addition, preferably, the base includes a cassette aperture located beneath the ball bearing assembly. The cassette aperture is suitable for receiving an X-ray cassette.

In accordance with further aspects of this invention, preferably, the ball bearing assembly includes a ball bearing having an inner race and an outer race separated by a plurality of balls mounted inside of a two piece toroidal case. One piece of the case is affixed to the base and the other piece supports the foot cup. Moreover, preferably, the calf restraining mechanism includes upper and lower calf braces. The lower calf brace is located near the ball bearing assembly and, thus, near the ankle of a patient's foot when it is mounted in the ankle stress machine. The upper calf brace is located such that it intersects the calf approximately midway up the calf. In addition, preferably, an ankle strap is provided to retain the foot in the foot cup.

In accordance with still further aspects of this invention, preferably, the stress supplied to the arm of the foot support and stress assembly is sensed by one or more strain gauges mounted on the arm. The strain gauge(s) is connected to an electric digital display instrument, such as a digital voltmeter, which is calibrated to display in units of force.

In accordance with yet still further aspects of this invention, the cassette aperture in the base is sized so as to receive approximately one-half of a standard X-ray cassette and the base and turntable protect adjacent regions of the cassette from X-rays. As a result, two X-ray pictures can be taken in a single cassette for comparison purposes by placing one-half of the cassette in the cassette aperture, positioning one ankle in the machine, stressing the ankle and taking an X-ray of the stressed ankle; and, then, placing the other half of the cassette in the cassette aperture and repeating the procedure for the other ankle of a patient.

As will be readily appreciated, the invention provides an uncomplicated mechanism for supporting the leg and foot of a patient and stressing the ankle in a manner that does not require a person be in the immediate vicinity of the ankle during the X-ray taking procedure. Since the amount of stress is measured, the same amount of inversion and eversion stress can be repetitively applied either to the same ankle, or to one ankle and then the other ankle for comparison. In addition to being used to stress an ankle during the taking of X-ray pictures, the ankle stress machine of the invention can be used to measure the amount of inversion and eversion stress that can be applied to a human ankle for other purposes. For example, an athlete's ankle is frequently "wrapped" prior to an athletic event. In the past various wrapping techniques have been utilized without detailed knowledge of the true benefit of available wrapping techniques. With the present invention various wrapping techniques can be compared with one another and with the strength of an unwrapped ankle to provide valuable information to athletes, coaches, physicians and the like for use in preventing ankle injuries.

BRIEF DESCRIPTION OF THE DRAWINGS

The foregoing objects and many of the attendant advantages of this invention will become more readily appreciated as the same becomes better understood by referecne to the following detailed description when taken in conjunction with the accompanying drawings wherein:

FIG. 1 is a pictorial view of a preferred embodiment of the invention;

FIG. 2 is a top plan view of the embodiment of the invention illustrated in FIG. 1; and, FIG. 3 is a side elevational view of the embodiment of the invention illustrated in FIGS. 1 and 2.

DESCRIPTION OF THE PREFERRED EMBODIMENT

The preferred embodiment of the invention illustrated in FIGS. 1-3 includes a base 11; a calf restraining mechanism 13; a turntable 15; a foot support and stress assembly 17; and, a stress measuring device 19. The base 11 includes a bottom plate 21, an upper plate 23 and a plurality of spacer bars 25a, b, c and d. The bottom and upper plates 21 and 23 are formed of sheet material, such as sheet metal, and are of generally the same rectangular size. The spacer bars 25a, b, c and d are orthogonally mounted (with respect to the longitudinal axis of the bottom and upper plates) between the bottom and upper plates 21 and 23. One spacer bar 25a and 25d is mounted near each end of the plates. The remaining spacer bars 25b and 25c are mounted inwardly of the end spacer bars 25a and 25d. One end spacer bar 25a and the adjacent inward spacer bar 25b define the edges of a cassette aperture 12 adapted to receive a standard X-ray cassette 14, loaded with a 10 inch×12 inch plate. Formed in the upper plate 23 in line with the cassette aperture 12 is a large circular hole 26. The spacer bars are attached to the bottom plate 21 by flat-head machine screws mounted in countersunk holes in the bottom plate. The upper plate 23 is attached to the spacer bars 25a, b, c and d by hex-head or flat-head machine screws, as required. Obviously, other attachment media can be used, if desired.

Mounted atop the base 11 on the end remote from the cassette aperture end is the calf restraining mechanism 13. The calf restraining mechanism 13 includes: a hat-shaped bracket 31; a Z-shaped bracket 33; an upper calf brace 35; and, a lower calf brace 37. The hat-shaped bracket is generally equal in length to the width of the upper plate 23 and is mounted near the end of the upper plate remote from the cassette aperture end of the base. Preferably, the hat-shaped bracket is formed of sheet metal and is adjustably attached to the upper plate 23 via four longitudinal slots 27 formed in the upper plate 23. More specifically, the longitudinal axis of the longitudinal slots 27 lie parallel to the longitudinal axis of the base and on either side thereof. The hat-shaped bracket is attached to the upper plate by four bolts 32 that pass through holes in the flanges of the hat-shaped bracket 31 and the slots 27. The bolts are threaded into the ends of two longitudinally oriented bars 34 located beneath the lower surface of the upper plate 23.

The top of the hat-shaped bracket 31 includes two pairs of slots 36 lying transverse to the longitudinal axis of the base 11. The upper calf brace 35, which is preferably formed of a band of sheet metal, is mounted atop the hat-shaped bracket 31. More specifically, the upper calf brace includes a curved region that is curved so as to conform to the upper area of the calf of a person. One end of the upper calf brace 35 angles away from the curved region and terminates in a planar flange. The planar flange includes a hook-shaped hole 38 that allows the upper calf brace to be bolted by a bolt 39 to one end or the other of one of a pair of elongate bars 40 mounted beneath the upper surface of the hat-shaped bracket 31. More specifically, the elongate bars lie transverse to the longitudinal axis of the base 11. One elongate bar extends between each pair of slots 36. The bars include threaded apertures at each end, which receive one of the bolts 39. Only one of the bolts is used to connect the upper calf brace 35 to the hat-shaped bracket 31. The other bolts allow the upper calf brace to be mounted in different positions and the slots provide for transverse adjustment. Except for the bolt 39 attaching the upper calf brace to the hat-shaped bracket, the other bolts can be loose. The elongate bars 40 are retained against the under surface of the hat-shaped bracket by a hat-shaped keeper 45 that spans the center of the elongate bars 40 and is riveted to the hat-shaped bracket 31.

The hook-shaped hole 38 allows the upper calf brace 35 to be unhooked from one bolt 39 and moved to one of the other bolts without removal of either bolt from its threaded aperture in the related elongate bar 40. This makes it possible to move the upper calf brace without first unscrewing the present attachment bolt 39 out of the related elongate bar 40, removing the upper calf brace 35, replacing the removed bolt 39, unscrewing a second bolt 39 and reinserting it into its related bar 40 after passing it through a hole in upper calf brace 35.

The Z-shaped bracket 33 is also formed of sheet metal and includes one flange connected to the upper plate 23 by the same machine screws that attach through the upper plate 23 to the spacer bar 25b that defines the inner edge of the cassette aperture 12. The web of the Z-shaped bracket 33 extends orthogonally away from the upper plate 23. The other flange of the Z-shaped bracket 33 overlies the adjacent area of the cassette aperture and includes a pair of slots 41 having a common longitudinal axis that lies orthogonal to the longitudinal axis of the base 11. The lower calf brace 37 is mounted atop the other flange of the Z-shaped bracket 33. More specifically, as with the upper calf brace 35, the lower calf brace 37 is preferably formed of a band of sheet metal and includes a curved region that conforms to the lower area of the calf of a person. One end of the lower calf brace 37 angles away from the curved region and terminates in a planar flange. The planar flange includes a hook-shaped hole 42 via which it is bolted by one or the other of a pair of bolts 43 threaded into the ends of a bar 44 mounted beneath the upper surface of the other flange of the Z-shaped bracket 33. The bar spans the region between the pair of slots 41 and is retained in place by a hat-shaped keeper 46 that spans the mid-region of the bar and is affixed to the Z-shaped bracket by rivets.

As it will be appreciated from the foregoing description the upper and lower calf braces 35 and 37 are position adjustable. The braces can be mounted on either side of their respective hat and Z-shaped support brackets 31 and 33. Regardless of which side they are mounted on, both braces are laterally adjustable with respect to the longitudinal axis of the base 11. Further, because the hat-shaped bracket 31 is longitudinally adjustable, the upper calf brace 35 is longitudinally position adjustable. The upper calf brace is also longitudinally adjustable with respect to the hat-shaped bracket 31. Because of these various adjustments, the calf restraining mechanism is adaptable to a wide variety of different sized calfs. It should be noted that the use of bars 34, 40 and 44, rather than nuts, provides ease of adjustment since wrenches are not required to hold nuts while the various bolts 32, 39 and 43 are being tightened. Rather, rotation of the bar is prevented by the use of a bolt on the end of the bar remote from the bolt being tightened, even if the former bolt is lose. Further, the hook-shaped slots eliminate the need to remove the bolts when brace repositioning is required, as discussed above.

The turntable 15 is mounted on the upper plate 23 and surrounds the large circular hole 26. More specifically, the turntable 15 includes a large ball bearing 53 mounted inside of a toroidal case 55. The central aperture in the toroidal case has a diameter equal to the diameter of the large circular hole 26. The toroidal case 55 has a rectangular cross-sectional configuration and comprises an inner L-shaped member 57 and an outer L-shaped member 59. The inner L-shaped member 57 includes a first leg that defines the periphery of the central aperture in the toroidal case and a second leg that extends outwardly from the first leg. The second leg is affixed to the upper plate 23 about the large circular hole 26. The outer L-shaped member 59 includes a first leg that lies parallel to the leg of the inner L-shaped member 57 attached to the upper plate 23 and a second leg that defines the outer periphery of the toroidal case. The large ball bearing 53 is mounted in the rectangular aperture defined by the inner and outer L-shaped members and rotatably connects the L-shaped members together. More specifically, the bearing 53 includes an inner race 61 that is affixed to the inner L-shaped member 57 of the case 55 and an outer race 63 that is affixed to the outer L-shaped member 59. The balls 65 of the ball bearing lie in grooves in the inner and outer races. As a result, the inner and outer L-shaped members are free to rotate with respect to one another, about the central axis of the toroidal case 55 and the large circular hole 26.

The foot support and stress assembly 17 includes a radial flange 71 affixed to the leg of the outer L-shaped member 59 of the toroidal case 55 lying parallel to the upper plate 23 of the base 11. Affixed to the radial flange 71 and the outer surface of the other leg of the outer L-shaped member 59 of the case 55 is a block 73. Extending radially outwardly (with respect to the central axis of the larger circular hole 26) from the block 73 is an arm 75. Preferably, the arm 75 has a square cross-sectional configuration. Mounted on the outer end of the arm 75 is a handle 77.

Mounted on the other side of the flange 71 is a bracket 79. The bracket 79 includes a pair of orthogonal plates 81 and 83 and three reinforcing ribs 85 extending between the plates 81 and 83. One plate 81 is affixed to the flange 71 by a series of bolts and nuts 87. The bolts extend through slots 89 formed in the flange 71. The slots lie parallel to the radial axis of the flange 71, on either side thereof. As a result, the bracket 79 is radially position adjustable.

Attached to the other plate 83 of the bracket 79 is a foot support 91. The foot support 91 includes a foot cup 93. The foot cup 93 is orthogonally oriented with respect to the plane of the base 11 and includes a cup-shaped region 94 configured to receive the heel of a patient's foot. The cup-shaped region merges into a planar region 96 having flared side walls 98 suitable for receiving the bottom and sides of a patient's foot. More specifically, the side walls 98 are adapted to impinge on the sides of a foot. The planar region 96 and side walls 98 extend outwardly from the heel region 94 to the end of the metatarsal bones of the largest foot to be accommodated by the ankle stress machine. Mounted on the side walls 98 above the heel region 94 are strap attachment brackets 100. The strap attachment brackets attach an ankle strap 102 to the foot cup 93. Preferably, the ankle strap includes a Velcro closure.

The cup-shaped region 94 of the foot cup 93 and the planar region 96 are attached to a pair of flanges 95 that extend orthogonally outwardly from the planar region. The flanges 95 are affixed to an attachment plate 97 that lies parallel to the planar region 96 of the foot cup 93. The attachment plate 97 is attached by bolts 99 to the plate 83 of the bracket 79. The bolts extend through slots in the plate 83 of the bracket 79 and are threaded into the attachment plate 97.

Mounted atop the end of the base, beneath the arm 75, is a protractor 101. The protractor has a center coincident with the center of the toroidal case 55 and the large circular hole 26. Imprinted along the outer periphery of the upper surface of the protractor is an angular scale, which coacts with the arm 75.

In operation, the ankle stress machine is first adjusted to conform to the patient's foot. The adjustments include positioning the foot cup by loosening bolts 99 and moving the foot cup until the center area of the patient's ankle lies along the axis of the large circular hole 26 in the upper plate 23 and the aperture in the toroidal case 55. The upper and lower calf braces 35 and 37 are adjusted so that the lower calf brace rests against what will be the outer side of the calf when the ankle is stressed in the manner hereinafter described. The upper calf brace is adjusted to rest against the inner side of the calf. Thus, the lower and upper calf braces rest against opposite sides of the calf. Preferably during machine adjustment the turntable is latched into a fixed position by a latch mechanism 103. The latch mechanism 103 includes an arm 104 hinged at its mid-region to the web of the Z-shaped bracket 33. One end of the arm 104 includes a pin 105 that extends through an aperture in the web. The pin 105 is adapted to be received by a hole in the outer L-shaped member 59 of the toroidal case 55 when the foot cup 93 is aligned with the longitudinal axis of the base 11. At this point the arm 75 lies over the zero degree (0°) mark on the protractor 101.

After the ankle stress machine has been adjusted for the patient's foot, the foot is strapped into the foot cup. As a result the heel is pressed into the cup-shaped region 94 and the bottom of the foot is pressed against the planar region 96. If not previously released, the latch 103 is then released. Thereafter, the technician, physician, nurse, etc., grasps the handle 77 and pulls the arm in the desired direction. This action applies rotational force about the axis of the large circular aperture 26 and thus about the ankle. As a result the ankle is stressed. The amount of stress force can be measured in any one of several well known ways. For example, strain gauges 106 can be mounted on the arm 75 and connected to a suitable electronic measuring and display device, such as a digital voltmeter 107. In a conventional manner the strain gauge detects the strain on the arm and the detected strain is converted into a force reading by the digital voltmeter, whose display, or course, is calibrated in terms of force. This type of measuring device is illustrated in block form in FIGS. 1 and 3. Alternatively, as illustrated in FIG. 2, a spring-loaded mechanical gauge 109 having a handle 108 located on one end and its opposite end connected to the arm 75 can be used to measure the applied force. Pulling on the handle 101 applies a force to the arm 75. This force is measured by the spring-loaded force measuring gauge in a conventional manner. Of course, for an accurate reading, the force axis vector must lie orthogonal to the longitudinal axis of the arm 75.

As noted above, a cassette aperture 12 is located in the base 11 between the upper plate 23, the bottom plate 21 and two of the spacer bars 25a and 25b, in alignment with the large circular hole 26. The cassette aperture is adapted to receive an X-ray cassette 14. Preferably, the cassette aperture is sized such that approximately one-half of an X-ray cassette can be positioned in alignment with the large circular hole 26. That is, the diameter of the large circular hole 26 and the aperture in the toroidal case 55 is somewhat less than one-half the width of the image area of one X-ray cassette. As a result, two X-rays can be taken on a single cassette for side-by-side comparison. In this regard, the region of the cassette not receiving the X-rays from the X-ray source 111 (FIG. 3) is protectfed from X-radiation by the ball bearing 53 and the toroidal case 55 of the turntable assembly and by the upper plate 23. As a result, an injured ankle can be compared with an uninjured ankle to determine the bone separation differences therebetween when the same amount of stress is applied to both ankles. The bone separation differences provide a doctor with information about the type and nature of the injury to the injured ankle.

As will be appreciated from the foregoing description the invention provides an ankle stress machine for stressing the ankle of the patient. The invention overcomes the disadvantages of prior art stressing techniques requiring that a person manually stressing an ankle be located close to the ankle while an X-ray is taken. Thus, the amount of person X-ray exposure is reduced, if not entirely eliminated. In addition, and more importantly because stress is measured by the present invention, the same amount of stress can be repetitively applied to the same ankle or to both ankles of a patient for comparison purposes. Further, if desired, angular measurement can also be made using the arm/protractor combination. Still further, stress and/or angle data can be written on the X-ray during the development process. This data can be compared with similar data written on earlier or later X-rays so that healing progress can be evaluated.

While a preferred embodiment of the invention has been illustrated and described, it will be appreciated that various changes can be made therein without departing from the spirit and scope of the invention. For example, said cylindrical, large diameter ball bearing could be replaced by a cylindrical, large diameter roller bearing, if desired. Consequently, the invention can be practiced otherwise than as specifically described herein.

The embodiments of the invention in which an exclusive property or privilege is claimed are defined as follows:

1. An ankle stress machine comprising:
a planar base;
calf restraining means mounted on said base for supporting a calf spaced from said planar base and restraining movement thereof in one direction in a predetermined plane;
a turntable, said turntable including a large cylindrical bearing mounted on said planar base so as to lie proximal to the ankle, when a calf is supported by said calf restraining means, said large cylindrical bearing having an axis of rotation lying orthogonal to said predetermined plane;
a foot support and stress assembly mounted on said turntable, said foot support and stress assembly including a foot cup positioned to receive a foot attached to a calf supported by said calf restraining means, said foot cup including a heel region for receiving the heel of said foot, a planar region for receiving the bottom of said foot and side walls for impinging on the sides of said foot, said planar and said side walls extending from said heel to the end of the metatarsal bones of said foot, said foot support and stress assembly also including an arm connected to said foot cup for rotating said turntable and, thus, said foot cup about the axis of rotation of said large cylindrical bearing; and,
stress measuring means connected to said arm for measuring the stress on said arm when said arm is stressed during the rotation of said turntable and, thus, said foot cup.

2. An ankle stress machine as claimed in claim 1 wherein said planar base includes an X-ray cassette aperture aligned with the aperture in said large cylindrical bearing.

3. An ankle stress machine as claimed in claim 2 wherein said calf restraining means includes a first bracket mounted on said planar base and a first calf brace mounted on said first bracket, said first calf brace including a curved region generally configured so as to conform the mid-region of a human calf and a second bracket mounted on said planar base adjacent said turntable so as to overlie said turntable and a second calf brace mounted on said second bracket, said second calf brace including a curved region configured so as to conform to the lower end of a human calf.

4. An ankle stress machine as claimed in claim 3 including a strap mounted on said foot cup for crossing the ankle of a foot positioned in said foot cup and pressing the heel of said foot into the heel region of said foot cup.

5. An ankle stress machine as claimed in claim 4 wherein said planar base includes upper and lower plates and wherein said upper plate includes a large circular hole aligned with the aperture in said large cylindrical bearing and, thus, with said X-ray cassette aperture in said planar base.

6. An ankle stress machine as claimed in claim 5 including a protractor mounted on said upper plate of said base beneath said arm, the rotational axis of said protractor being coincident with the rotational axis of said large cylindrical bearing.

7. An ankle stress machine as claimed in claim 6 wherein said turntable includes a toroidal housing formed of first and second L-shaped members, one of said L-shaped member being attached to said upper plate of said base so as to surround said large circular hole in said upper base, said foot cup and said arm being attached to said second L-shaped member, said first and second L-shaped members being connected together by said large cylindrical bearing.

8. An ankle stress machine as claimed in claim 7 wherein said force measuring means is an electronic force measuring means.

9. An ankle stress machine as claimed in claim 8 wherein said electronic force measuring means includes a strain gauge attached to said arm and an electronic measuring instrument for measuring the strain detected by said strain gauge and providing an output calibrated in terms of force.

10. An ankle stress machine as claimed in claim 7 wherein said force measuring means includes a mechanical force measuring device attached to said arm.

11. An ankle stress machine as claimed in claim 1 wherein said calf restraining means includes a first bracket mounted on said planar base and a first calf brace mounted on said first bracket, said first calf brace including a curved region generally configured so as to conform the mid-region of a human calf and a second bracket mounted on said planar base adjacent said turntable so as to overlie said turntable and a second calf brace mounted on said second bracket, said second calf brace including a curved region configured so as to conform to the lower end of a human calf.

12. An ankle stress machine as claimed in claim 1 wherein said planar base includes upper and lower plates and wherein said upper plate includes a large circular hole aligned with the aperture in said large cylindrical bearing and, thus, with said X-ray cassette aperture in said planar base.

13. An ankle stress machine as claimed in claim 1 wherein said turntable includes a toroidal housing formed of first and second L-shaped members, one of said L-shaped member being attached to said upper plate of said base so as to surround said large circular hole in said upper base, said foot cup and said arm being attached to said second L-shaped member, said first and second L-shaped members being connected together by said large cylindrical bearing.

14. An ankle stress machine as claimed in claim 1 wherein said force measuring means is an electronic force measuring means.

15. An ankle stress machine as claimed in claim 14 wherein said electronic force measuring means includes a strain gauge attached to said arm and an electronic measuring instrument for measuring the strain detected by said strain gauge and providing an output calibrated in terms of force.

16. An ankle stress machine as claimed in claim 1 wherein said force measuring means includes a mechanical force measuring device attached to said arm.

* * * * *